(12) United States Patent
Stephens et al.

(10) Patent No.: US 8,367,122 B2
(45) Date of Patent: Feb. 5, 2013

(54) CONTROL OF BLOOD VESSEL PHYSIOLOGY TO TREAT SKIN DISORDERS

(75) Inventors: Laura Stephens, Danvers, MA (US); John J. Masiz, Topsfield, MA (US); Stephen G. Carter, Andover, MA (US); Zhen Zhu, Tewksbury, MA (US); Kanu Patel, Londonderry, NH (US)

(73) Assignee: BioChemics, Inc., Danvers, MA (US)

( * ) Notice: Subject to any disclaimer, the term of this patent is extended or adjusted under 35 U.S.C. 154(b) by 0 days.

(21) Appl. No.: 12/483,073

(22) Filed: Jun. 11, 2009

(65) Prior Publication Data

US 2010/0003353 A1   Jan. 7, 2010

Related U.S. Application Data

(60) Provisional application No. 61/060,543, filed on Jun. 11, 2008.

(51) Int. Cl.
*A61K 36/886* (2006.01)
(52) U.S. Cl. ............. 424/725; 424/744; 424/401; 607/1
(58) Field of Classification Search ........................ None
See application file for complete search history.

(56) References Cited

U.S. PATENT DOCUMENTS

| | | | |
|---|---|---|---|
| 4,440,777 A | 4/1984 | Zupan | 424/274 |
| 4,933,184 A | 6/1990 | Tsuk | 424/449 |
| 5,229,130 A | 7/1993 | Sharma et al. | 424/449 |
| 5,460,821 A | 10/1995 | Masiz | 424/449 |
| 5,645,854 A | 7/1997 | Masiz | 424/449 |
| 5,853,751 A | 12/1998 | Masiz | 424/449 |
| 5,895,649 A | 4/1999 | De Lacharriere et al. | 424/130 |
| 5,895,658 A | 4/1999 | Fossel | 424/401 |
| 5,922,332 A | 7/1999 | Fossel | 424/401 |
| 5,932,215 A | 8/1999 | De Lacharriere et al. | 424/158.1 |
| 6,207,713 B1 | 3/2001 | Fossel | 514/565 |
| 6,306,130 B1 | 10/2001 | Anderson et al. | 606/27 |
| 6,458,841 B2 | 10/2002 | Fossel | 514/565 |
| 6,486,206 B1 | 11/2002 | Lurie | 514/561 |
| 6,635,274 B1 | 10/2003 | Masiz et al. | 424/449 |
| 7,105,172 B1 | 9/2006 | Bolla | 424/400 |
| 7,179,789 B2 | 2/2007 | Patt | 514/6 |
| 7,192,616 B2 | 3/2007 | Cals-Grierson et al. | 424/769 |
| 2003/0091659 A1* | 5/2003 | Lu et al. | 424/727 |
| 2003/0104043 A1* | 6/2003 | Brown et al. | 424/450 |
| 2005/0256204 A1 | 11/2005 | Bitter, Sr. | 514/649 |
| 2005/0271596 A1* | 12/2005 | Friedman et al. | 424/45 |
| 2006/0057081 A1 | 3/2006 | Boxrud | 424/59 |
| 2006/0217690 A1 | 9/2006 | Bastin et al. | 606/9 |
| 2008/0312296 A1 | 12/2008 | Carter et al. | 514/356 |
| 2009/0053290 A1 | 2/2009 | Sand et al. | 424/449 |
| 2009/0221536 A1 | 9/2009 | Fossel | 514/162 |

FOREIGN PATENT DOCUMENTS

| | | |
|---|---|---|
| EP | 1621192 | 2/2006 |
| WO | WO 01/17498 | 3/2001 |
| WO | WO 2005/102282 | 11/2005 |
| WO | WO 2005/123190 | 12/2005 |
| WO | WO 2007/086395 | 8/2007 |
| WO | WO 2007/103555 | 9/2007 |
| WO | WO 2008/054059 | 5/2008 |
| WO | WO 2008/109124 | 9/2008 |

OTHER PUBLICATIONS

Goldberg (Clinics in Plastic Surgery (2000), vol. 27, No. 2, pp. 173-180).*
http://www.wiseacre-gardens.com/plants/perennial/bugleweed.html—accessed Oct. 2010.*
Jesitus (Dermatology Times (Mar. 2005), vol. 26, pp. 66-67).*
Kautz, G., et al., "Management of Rosacea with Intense Pulsed Light (IPL) Systems and Laser" Medical Laser Application 23 (2008) 65-70.
McGill, D J., et al., "The Effect of Ambient Temperature on Capillary Vascular Malformations" British Journal of Dermatology, vol. 154, (2006), pp. 896-903.
Albayrak, Timur Authorized Officer—European Patent Office, *The International Search Report and Written Opinion*, International Application No. PCT/US2009/047098, International Searching Authority, Aug. 27, 2009, 12 pages.
Svaasand LO, et al., "Increase of Dermal Blood Volume Fraction Reduces the Threshold for Laser-Induced Purpura: Implications for Port Wine Stain Laser Treatment" Norwegian University of Science and Technology, No. 7491, Laser in Surgery and Medicine, vol. 34, 2004, pp. 182-188.
Nase, G., et al., "The Latest Advances in Rosacea Treatment: Triple-Pass Laser Treament" Dermatology Times, Jun. 1, 2005.

* cited by examiner

*Primary Examiner* — Susan Hoffman
(74) *Attorney, Agent, or Firm* — Sunstein Kann Murphy & Timbers LLP

(57) ABSTRACT

In a method for treating an affected skin region of a patient having a skin disorder, a vasodilation composition is applied to an affected skin region of a patient, the affected skin region exhibiting a skin disorder characterized by at least one abnormal blood vessel, and the affected skin region is then treated so as to non-invasively disrupt tissue architecture, e.g., by inducing ischemia, of the at least one abnormal blood vessel. A vasoconstriction composition can then be applied to the skin region to cause vasoconstriction of the at least one blood vessel in order to promote healing.

18 Claims, 3 Drawing Sheets

| | Visia Before | Treatment Date | Visia After | Left # of Reds Before | Left # of Reds After | Left % Change | Did Left Visia Improve | Did left Photos Improve | Right # of Reds Before | Right # of Reds After | Right % Change | Did Right Visia Improve | Did Right Photos Improve | Is Left % Better Than Right |
|---|---|---|---|---|---|---|---|---|---|---|---|---|---|---|
| 1 | 8/22/2007 | 8/27/2007 | 9/24/2007 | 67 | 54 | 19% | yes | yes | 74 | 71 | 4% | yes | yes | yes |
| 2 | 8/28/2007 | 8/30/2007 | 9/27/2007 | 118 | 93 | 21% | yes | yes | 124 | 107 | 14% | yes | yes | yes |
| 3 | 8/24/2007 | 9/5/2007 | 10/4/2007 | 235 | 193 | 18% | yes | yes | 188 | 170 | 10% | yes | yes | yes |
| 4 | 9/10/2007 | 9/10/2007 | 10/11/2007 | 109 | 122 | -12% | no | yes | 129 | 141 | -9% | no | yes | no |
| 5 | 9/6/2007 | 9/19/2007 | 10/23/2007 | 128 | 133 | -4% | no | yes | 111 | 138 | -24% | no | yes | yes |
| 6 | 9/13/2007 | 9/13/2007 | 10/18/2007 | 183 | 159 | 13% | yes | yes | 182 | 180 | 1% | yes | yes | yes |
| 7 | 9/6/2007 | 9/19/2007 | 10/23/2007 | 122 | 124 | -2% | no | yes | 109 | 134 | -22% | no | yes | yes |
| 8 | 8/28/2007 | 10/4/2007 | 11/3/2007 | 123 | 111 | 10% | yes | yes | 118 | 100 | 15% | yes | yes | no |
| 9 | 8/24/2007 | 10/6/2007 | 11/6/2007 | 90 | 122 | -35% | no | yes | 107 | 109 | 2% | yes | yes | no |
| 10 | 9/6/2007 | 10/17/2007 | 11/15/2007 | 149 | 140 | 6% | yes | yes | 142 | 129 | 9% | yes | yes | no |
| 11 | 8/23/2007 | 10/4/2007 | 10/31/2007 | 155 | 112 | 28% | yes | yes | 152 | 130 | 14% | yes | yes | yes |
| 12 | 10/18/2007 | 10/18/2007 | 11/20/2007 | 132 | 112 | 15% | yes | yes | 160 | 149 | 7% | yes | yes | yes |
| 13 | 9/20/2007 | 10/30/2007 | 11/26/2007 | 80 | 80 | 0% | no | yes | 68 | 52 | 24% | yes | yes | no |
| 14 | 11/26/2007 | 11/26/2007 | 12/20/2007 | 151 | 115 | 24% | yes | yes | 130 | 93 | 28% | yes | yes | no |
| 15 | 11/27/2007 | 11/27/2007 | 1/10/2008 | 121 | 101 | 17% | yes | yes | 118 | 95 | 19% | yes | yes | no |
| 16 | 11/20/2007 | 1/3/2008 | 1/30/2008 | 147 | 82 | 44% | yes | yes | 130 | 100 | 23% | yes | yes | yes |

FIG. 3

CONTROL OF BLOOD VESSEL PHYSIOLOGY TO TREAT SKIN DISORDERS

REFERENCE TO RELATED APPLICATION

This application claims benefit of the filing date of U.S. provisional application Ser. No. 61/060,543, filed Jun. 11, 2008, hereby incorporated by reference.

TECHNICAL FIELD

The invention relates to compositions and methods for treating skin disorders.

Background

Rosacea is a hereditary, chronic skin disorder that causes slight to severe redness and is often characterized by flare-ups and remissions. Rosacea primarily affects facial blood vessels. Rosacea is more frequently diagnosed in women, but tends to be more severe in men. The disorder typically begins after age 30 as a flushing or redness on the cheeks, nose, chin or forehead that may come and go. Over time, the redness tends to become ruddier and more persistent, and visible blood vessels may appear. In severe cases, rosacea skin can become inflamed and erupted. The affected skin tissue may swell and thicken, becoming sensitive to touch.

Since rosacea affects mainly the face, sufferers often have lowered self-confidence and self-esteem, avoiding public contact or cancelling social engagements. Some sufferers also experience erythrophobia, a morbid fear of having a red face and being embarrassed in public by it.

During episodes, experts agree that vascular abnormalities are central to all stages and symptoms of rosacea. The blood vessels become hyper-responsive to internal and external stimuli including sun exposure, alcohol, medications, stress, emotions and aging of the skin. This hyper-responsiveness results in increased blood flow through the facial skin. One or all three of the following functional changes may take place in blood vessels affected by rosacea: dilation in response to a substance that normal blood vessels do not respond to, over-dilation, or dilation for an abnormally extended period of time.

In addition to functional changes, affected blood vessels may undergo extensive structural changes. Such structural changes may include:
a) Permanent dilation of blood vessels (telangiectasia): Clinical studies on rosacea sufferers demonstrate that a significant portion of facial blood vessels are 'broken'; these vessels are permanently fixed in a dilated state.
b) Damage to vascular smooth muscle: In rosacea sufferers, the muscular layer of facial blood vessels is often found to be damaged and abnormally thin.
c) Damage to endothelial cells: In rosacea sufferers, the inner layer of the blood vessel wall is often found to be severely damaged and dysfunctional.
d) Growth of new vessels: abnormal growth of new blood vessels may occur in rosacea sufferers.
e) Orientation of blood vessels closer to the surface of facial skin: medical reports on rosacea sufferers indicate that blood vessels may become oriented so that they are closer to the surface of the facial skin.
f) Abnormal fusion of blood vessels.

The functional changes usually occur first, causing the flushing and ruddiness. Over time, this functional hyper-responsiveness may lead to increased blood vessel damage and subsequent structural changes. This results in more blood flow through the facial skin—causing more inflammation and damage—making rosacea a chronic and progressive disease.

Conventional treatment of rosacea and other vascular lesions include topical treatments with antibiotics, sulfa preparations, and topical steroids and avoidance of triggers such as heat, cold, sunlight, alcohol, emotions and stress. These treatments are temporary as none of these treatments removes the abnormal vessels.

SUMMARY OF THE INVENTION

In a first embodiment of the invention there is provided a method for treating an affected skin region of a patient having a skin disorder, the method including a) applying a vasodilation composition to an affected skin region of a patient, the affected skin region exhibiting a skin disorder characterized by at least one abnormal blood vessel, and b) disrupting the tissue architecture of the at least one abnormal blood vessel. Vasodilation is applied to the affected skin region for a time sufficient to induce vasodilation of the at least one abnormal blood vessel in the affected skin region.

An "abnormal blood vessel" is understood to mean a blood vessel that exhibits one or more of the following functional and/or structural characteristics:
1) blood vessels which are hyper-responsive to internal and external stimuli, e.g., sun exposure, alcohol, medication, stress, emotion, or aging of the skin, resulting in increased blood flow through the skin;
2) blood vessels which are dilated in response to a substance that normal blood vessels do not respond to, which are overly-dilated, or which are dilated for an abnormally extended period of time;
3) blood vessels which are permanently dilated;
4) blood vessels in which the smooth muscle is damaged or abnormally thin;
5) blood vessels in which the endothelial cells are damaged or dysfunctional;
6) blood vessels which are new growth blood vessels in locations where new growth blood vessels do not normally appear;
7) blood vessels which become oriented abnormally close to the skin relative to normal blood vessels in like anatomical location; and
8) blood vessels which are abnormally fused relative to normal blood vessels in like anatomical location.

Skin disorders characterized by at least one abnormal blood vessel include without limitation vascular legions, rosacea, telangiectasia, spider veins, varicose veins, actinically damaged skin, venous hypertension, Poikiloderma vasculare atrophicans, vascular malformations, and hemangioma. Such skin disorders occur in patients who are, e.g., human patients. Where the patient is a non-human mammal, e.g., a dog, cat, horse or other mammal, or when the patient is a bird, the various embodiments of the invention are useful as veterinary methods of treatment.

The term "vasodilation" refers to the dilation, e.g., by widening or by other means, of blood vessels. Vasodilators useful in the various embodiments of the invention include, e.g., arginine, preferably L-arginine. Other useful vasodilators include tolazoline, methyl nicotinate, and nitroprusside. In one embodiment, a vasodilation composition may be formulated to include arginine HCl, urea, glycerin, hydroxyethylcellulose, allantoin, and methylisothiazolinone.

In other related embodiments, the vasodilation composition can include arginine, preferably L-arginine, in the range of 0.001% to 10.0% w/w, e.g., 0.01% to 10.0% w/w. The method can include allowing a wait time sufficient for the vasodilation composition to cause dilation of the affected, i.e., abnormal, blood vessels prior to introducing the energy, such time referred to herein as a "vasodilation time".

In at least one embodiment, non-invasively disrupting the tissue architecture of the at least one abnormal blood vessel includes disruption of interactions between endothelial cells in the walls of the blood vessel. In some cases, without limitation, disruption of endothelial interactions can lead to collapse of the blood vessel. In some cases, disruption of endothelial interactions can further lead to ischemia of the blood vessel. In other cases, disrupting the tissue architecture of the at least one abnormal blood vessel, e.g., by disrupting endothelial cell interactions, can lead to re-orientation or re-arrangement of abnormal blood vessels.

By "non-invasive" is meant a procedure that is performed on a blood vessel without exposing the blood vessel surgically, and without the device used to perform the procedure, e.g., a device that heats, compresses, or rearranges the blood vessel tissue, directly contacting the blood vessel tissue. For example, a device can be used that delivers energy to the vessel through surrounding tissue, without touching the vessel itself.

In some embodiments, the tissue architecture of the at least one abnormal blood vessel can be disrupted by selectively heating the abnormal blood vessels by raising the temperature of the abnormal blood vessels relative to the temperature of surrounding tissue.

The process of disrupting the tissue architecture of the abnormal blood vessels, e.g., by non-invasive induction of ischemia, is frequently referred to herein as the "treatment" step. It can be accomplished by, without limitation, introducing energy to the abnormal blood vessels, e.g., by exposing the affected skin region to electromagnetic radiation, such as by photothermolysis, or to ultrasound and/or radio frequency radiation. Additional methods of non-invasive induction of disruption of abnormal blood vessel tissue architecture are known to those skilled in the art.

Thus, in some embodiments, non-invasively inducing ischemia includes administering a non-invasive treatment which selectively heats a target blood vessel to cause ischemia (or, in the case of already ischemic blood vessels, to increase ischemia), followed by cell death and degradation. One non-invasive method of inducing ischemia is to apply an external energy source that is capable of delivering energy in a wavelength preferentially absorbed by a blood vessel, as opposed to surrounding tissues, thereby selectively heating and thermo-damaging the walls of the blood vessel relative to the surrounding tissue.

After disrupting the tissue architecture of abnormal blood vessels, it is advantageous for the invention to optionally include applying a vasoconstriction composition to the affected skin region so as to cause vasoconstriction of the at least one blood vessel.

The term "vasoconstriction" refers to constriction, e.g., narrowing, of blood vessels. Vasoconstrictors useful in the various embodiments of the invention include, e.g., phytonin. Other useful vasoconstrictors include phenyl epinephrine, caffeine, butcher's bloom extract, and bugleweed extract. Without limitation, one particular embodiment of a vasoconstrictor formulation includes phytonin, aloe vera juice, arnica extract, cypress extract, Solomon's seal extract, a glyceryl stearate and peg-100 stearate, sodium palmitoyl proline, nymphaea alba flower extract, cyclomethicone, stearic acid, glycerin, cetyl alcohol, butcher's broom extract, bugleweed extract, triethanolamine, pomegranate oil, allantoin, methylisothiazolinone, grapefruit oil, and an alkyl acrylate crosspolymer.

In another embodiment of the invention there is provided a kit which is supplied to a patient, or to a health care provider or cosmetologist treating a patient. The kit can include, without limitation, a first topical skin formulation including a vasodilation composition, and a second topical skin formulation including a vasoconstriction composition. The kit can include written instructions for use, by or on a patient, of the first topical skin formulation prior to receipt by the patient of a treatment that non-invasively disrupts tissue architecture of an abnormal blood vessel, e.g., by a non-invasive ischemia-inducing treatment, and of the second topical skin formulation after receipt by the patient of a treatment that non-invasively disrupts tissue architecture of an abnormal blood vessel, e.g., by a non-invasive ischemia-inducing treatment. Other components can optionally be added to the kit, such as topical compositions to be applied while treating to disrupt tissue architecture, e.g., inducing ischemia, such as, e.g., a pain medication in a topical formulation.

Methods of the invention enhance treatment, e.g., thermolysis treatment, for various vascular skin disorders, by increasing the number and size of targeted blood vessels, optionally encouraging degradation and absorption of the necrotic tissue, and promoting healing. The embodiments of the invention provide numerous advantages. For example, applying the pre-treatment vasodilator to the skin increases the number of blood vessels that the treatment is able to target. Small blood vessels that would not contain enough blood to be photothermolysis targets without the enhanced flow induced by the pre-treatment vasodilator would otherwise be missed by the energy source. Thus, embodiments of the invention can prevent tiny abnormal blood vessels from becoming large abnormal vessels that will require further treatment.

Another advantage of applying a vasodilator to the skin prior to treatment to disrupt blood vessel tissue architecture, e.g., induce ischemia, e.g., with an energy source, is increased blood flow to blood vessels. Blood is the selective target for the energy source, so this results in larger cross sectional areas to be targeted within a blood vessel and more energy to be focused within that area to enhance ischemia of the blood vessel.

Yet another advantage of applying a vasodilator to the skin prior to treating to disrupt blood vessel tissue architecture, e.g., induce ischemia, is that vasodilatation of the blood vessels causes the endothelial wall of the blood vessel to stretch and decrease in thickness. Thinner blood vessels are more easily damaged by the photothermolysis process than normal vessels, enhancing the effect of photothermolysis and increasing ischemia.

An advantage of applying a vasoconstrictor to the affected area after treating to induce ischemia is that vasoconstrictors enhance the degradation of the ischemic blood vessel causing the vessels to shrink and collapse. Further advantages of applying a post treatment vasoconstrictor are that (1) anti-inflammatory agents in the formulation promote healing; and (2) the formulation contains skin-soothing agents that help to alleviate the sometimes painful effects of the process of inducing ischemia, such as by energy treatment.

An advantage of some embodiments of the present invention is that the number of treatment sessions, e.g., photothermolysis treatment sessions, needed is reduced compared to energy treatment carried out in the absence of the application of a pre-treatment vasodilator, resulting in decreased treatment costs for patients, fewer visits to the doctor's office by patients, and greater numbers of patients that can be treated by each doctors.

The methods of the various embodiments of the invention are simple, non-invasive, more effective than prior methods, and enhance the results of each treatment to induce ischemia. Such methods are safe and effective. The topical formulations are easy to apply and glide easily over the skin.

BRIEF DESCRIPTION OF THE DRAWINGS

The foregoing features of the invention will be more readily understood by reference to the following detailed description, taken with reference to the accompanying drawings, in which:

FIG. 3 is a chart showing the results of a clinical trial of an embodiment of the invention.

DETAILED DESCRIPTION

Embodiments of the present invention relate to compositions and methods for treatment of skin disorders. In specific illustrative embodiments, the compositions and methods are used for the treatment of rosacea, and for the treatment of skin disorders involving vascular lesions. Embodiments of the invention can also be used in the treatment of spider veins, varicose veins, actinically damaged skin, venous hypertension, Poikiloderma vasculare atrophicans, vascular malformations, hemangioma and telangiectasia.

In specific embodiments, topically applied vasodilator agents increase the blood flow to a targeted area prior to treatment. A targeted energy source then induces ischemia of blood vessels in the area. A subsequent topical application of a vasoconstrictor or anti-inflammatory composition can then be applied to promote healing or ameliorate discomfort.

In an embodiment, a composition of an embodiment of the invention can be a topical formulation, to be applied topically to the region of skin to be treated. By way of example, a vasodilation composition or a vasoconstrictor composition can be in any delivery form known to those of ordinary skill in the art as appropriate for application to the skin, including a cream, lotion, ointment, foam, or gel. In other embodiments, a composition of the invention can be applied by a patch.

Figure 1:
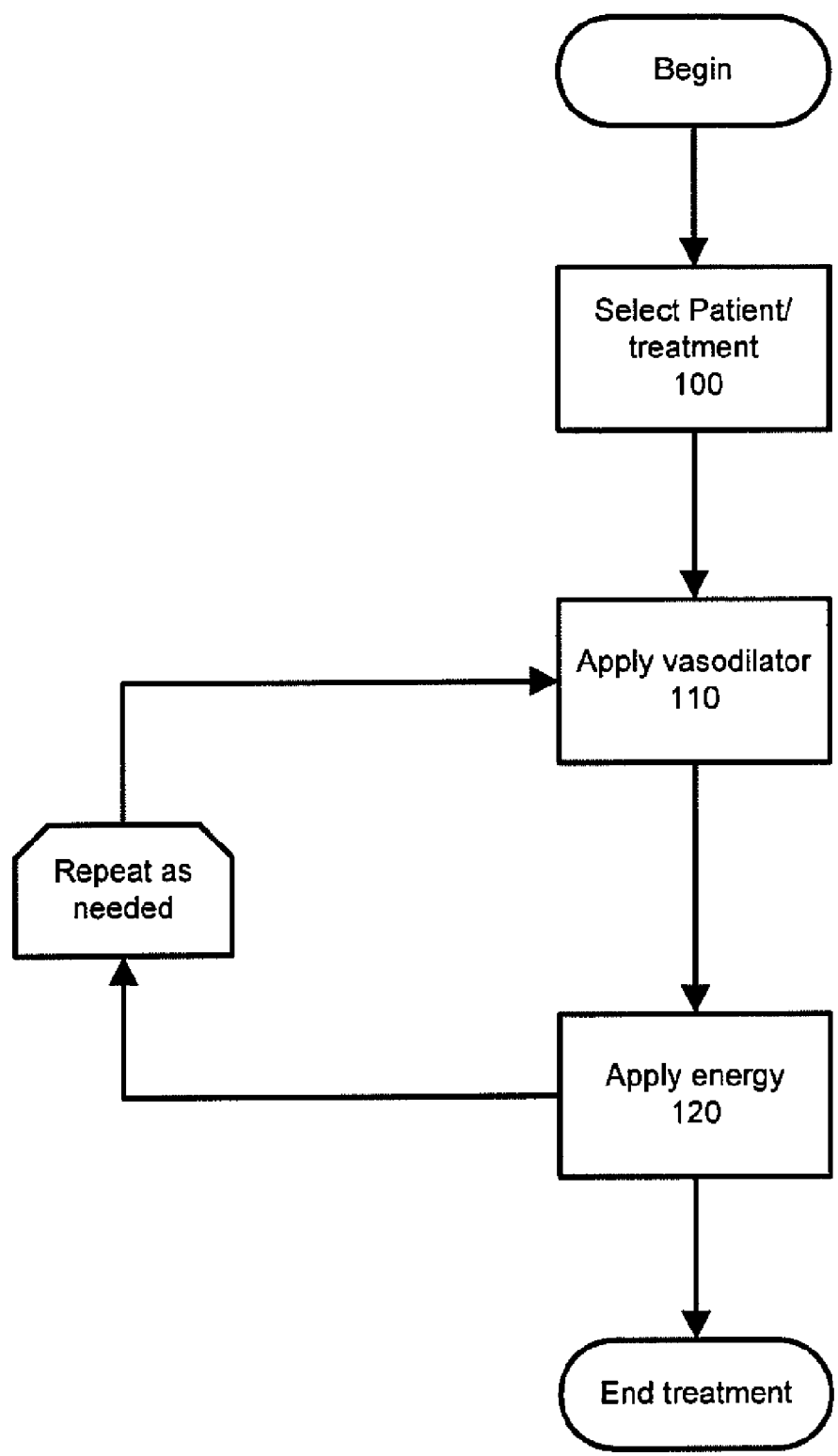
FIG. 1 is a flow diagram illustrating a method in accordance with an embodiment of the present invention.

FIG. 1 shows a flow chart in accordance with an embodiment of the invention. A patient with rosacea or other disorder characterized by one or more abnormal blood vessels is selected as a suitable candidate for treatment (step 100). A vasodilator is applied (e.g., rubbed into) to an affected skin region of the patient (step 110). The vasodilator may be a topically applied composition which contains an active ingredient that causes vasodilatation of a blood vessel. Depending on the vasodilation composition used and other relevant factors, a vasodilation time is allowed for the blood vessel or vessels to become dilated (e.g., 5 to 10 minutes). This vasodilation time can be a fixed amount of time, or sufficient time can be allowed, e.g., while the patient is being monitored, for indications that the blood vessels have dilated, prior to proceeding to the treatment step of inducing ischemia, e.g., by introducing energy.

In one embodiment, the vasodilator active ingredient in the vasodilation composition can be L-arginine, which may be included in a concentration range of 0.001% to 10%, e.g., 0.01% to 10.0% w/w, with the balance made of inactive ingredients or other active ingredients.

In the alternative or in combination with L-arginine, the vasodilation composition can include other active vasodilation ingredients known to those of ordinary skill in the art. Examples of such vasodilating agents include ginger extract, *ginkgo biloba*, hawthorne extract, bamethan sulphate, bencyclane fumarate, benpurodil hemisuccinate, benzyl nicotinate, buflomedil hydrochloride, buphenine hydrochloride, butalamine hydrochloride, cetledil citrate, ciclonicate, cinepazide maleate, cyclandelate, di-isopropylammonium dichloroacetate, ethyl nicotinate, hepronicate, hexyl nicotinate, Ifenprodil tartrate, inositol nicotinate, isoxsuprine hydrochloride, kallidinogenase, methyl nicotinate, maftidropuryl oxalate, nicametate citrate, niceritrol, nicobuxil, nicofuranose, nicotinyl alcohol, nicotinyl alcohol tartrate, nonidamide, oxpentifylline, papaveroline, pentifylline, pipratecol, propentofylline, raubasine, suloctidil, teasuprine, thymoxamine hydrochloride, tolazoline, xanthinol nicotinate, diazoxide, hydralazine, minoxidil, centrally acting agents including clonidine, quanaberz and methyl dopa, alpha-adrenoceptor agents including indoramin, phenoxybenzamine, phentolamine and prazosin, adrenergic neuron blocking agents including bethanidine, debrisoquine and guanethidine, ACE inhibitors including benazepril, captopril, cilazapril, enalapril, fosinopril, lisinopril, perindopril, quinapril and ramipril, ganglion-blocking agents including pentolinium and trimetaphan, calcium-channel blockers including amlodipine, diltiazem, felodipine, isradipine, nicardipine, nifedipine, nimodipine and verapamil, prosteglandins including prostacyclin, thrombuxane A2 leukotrienes, PGA, PGA1 PGA2 PGE1 PGE2 PGD, PGG and PGH, and angiotension II analogs including saralasin. Other suitable vasodilators include nitroglycerin, labetalol, thrazide, isosorbide dinitrate, pentaerythritol tetranitrate, digitalis, hydralazine, diazoxide and sodium nitroprusside, in a concentration range of 0.001 to 10.0% w/w, e.g., 0.01% to 10.0% w/w.

The vasodilation composition can be administered in a formulation that further includes substances that improve penetration or bioavailability of the active vasodilation ingredients. For example, the vasodilation composition can include a combination of phospholipids, fatty acids, chemical penetration enhancers and binding components that result in enhanced diffusion of the active ingredient into and through the stratum corneum.

The non-active ingredients of the vasodilation formulation can be selected from those known in the art, including distilled water, urea, propylene glycol, acrylates/c10-30 alkyl acrylate crosspolymer, allantoin, DMDM hydantoin, methylparaben, and excipients known to those skilled in the art as useful for formulating pharmaceutical preparations in a concentration range of 0.001% to 10.0% w/w., e.g., 0.01% to 10.0% w/w.

After vasodilation, energy is introduced into the dilated blood vessels (step 120). The energy can be in the form of electromagnetic radiation, such as pulsed and non-pulsed laser light or non-coherent light, e.g., at a wavelength range of 30 to 1100 nanometers, or, e.g., a wavelength of 500 to 1100 nanometers. One process of using light energy to induce selective heating and ischemia is known in the art as photothermolysis, where light energy is absorbed by chromophores in hemoglobin and oxyhemoglobin and is converted to heat. This selective heating increases the temperature in the red blood cells in the endothelium of the blood vessel wall causing ischemia, cell death and re-absorption of the blood vessel by the body.

Alternatively, energy can be introduced in the form of ultrasound or in the form of radio-frequency electromagnetic radiation. The applied energy is introduced with the objective of inducing ischemia of one or more blood vessels in the affected skin region.

In some embodiments, energy is supplied in the form of visible light that is preferentially absorbed by the blood vessel or its contents. For example, the light can be of a wavelength that is preferentially absorbed by hemoglobin carried in the blood vessels. The light energy absorbed by the hemoglobin is converted to thermal energy, thereby raising the local temperature and causing ischemia, cell death and eventual re-absorption of the blood vessel by the body. For example, the source of the light can be a pulsed dye laser, diode laser, Er:YAG laser, Nd:YAG laser, xenon flash lamp, alexandrite laser, semiconductor diode, copper vapor laser, argon ion laser, krypton ion laser, or other suitable light and/or laser source known to those skilled in the art.

Multiple photothermolysis treatments are often required due to eruption of new vascular lesions and reperfusion of energy-treated vessels. Reperfusion is the restoration of blood supply to tissue which is ischemic. Reperfusion is undesirable as it reduces the effectiveness of the treatment.

Additional methods, techniques, and compositions are known to the art; see, e.g., U.S. 2006/0217690 A1, "Method for Treating Various Dermatological and Muscular Conditions Using Electromagnetic Radiation", hereby incorporated by reference; U.S. Pat. No. 6,306,130 B1, "Apparatus and Methods for Removing Blood Vessels", hereby incorporated by reference.

Without wanting to be bound by scientific explanation, as a result of applying the vasodilator before irradiation, a larger number of blood cells may be present in the blood vessel, thereby increasing the efficiency of treatment. Additionally, the vasodilation step may make the application of energy more efficient with regard to induction of ischemia due to thinning of the vessel walls. Vasodilation may also increase the ability of the applied energy to target smaller vessels that might otherwise evade treatment. If left untreated, the smaller vessels would cause unwanted future pathologies, requiring further treatment and additional expense.

The process of FIG. 1 may be repeated as necessary.

Figure 2:
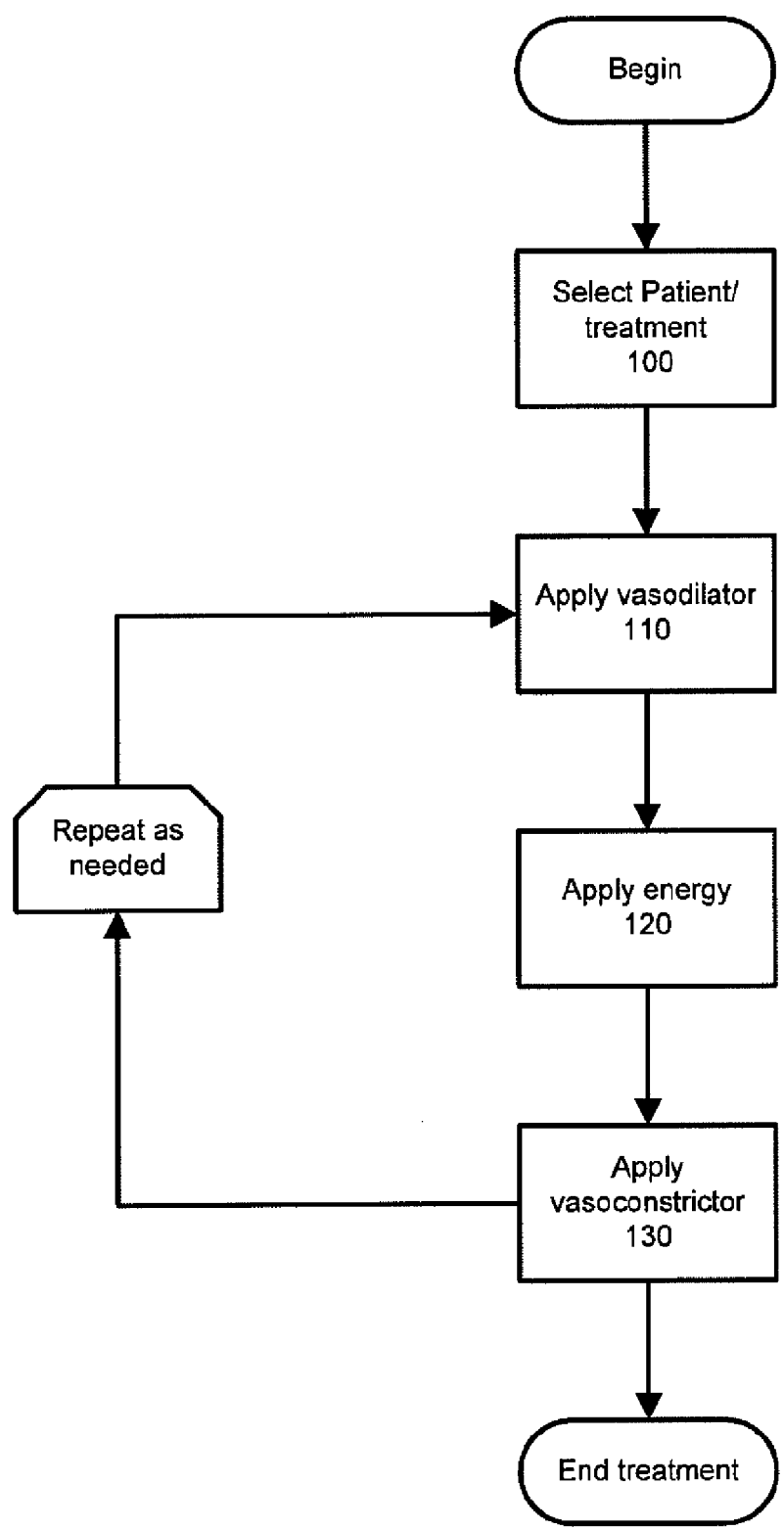
FIG. 2 is a flow diagram illustrating a method in accordance with another embodiment of the present invention.

FIG. 2 shows a flow chart in accordance with another embodiment of the invention. In this embodiment, after applying energy, a vasoconstrictor is applied (step 130). Like the vasodilator, the vasoconstrictor may be applied as a topical formulation. The application of the vasoconstrictor can confer one or more of the benefits of enhancing degradation of ischemic blood vessels, promoting healing, and alleviating pain. The vasoconstrictor formulation may also include anti-inflammatory, anti-edemic, analgesic, or other substances known in the art to promote healing or to enhance patient comfort.

In one embodiment, the vasoconstrictor composition formulation can include phytonin. Preferably, phytonin is present in a vasoconstrictor formulation within a concentration range of 0.001% to 10.0% w/w., e.g., 0.01% to 10.0% w/w.

In the alternative or in combination with phytonin, the vasoconstriction composition can include other active vasoconstriction ingredients known to those of ordinary skill in the art. Examples of such vasoconstricting agents include phenyl-epinephrine and caffeine. Additional examples of vasoconstricting agents include arnica extract, cypress extract, Solomon's seal extract, nymphaea alba flower extract, butcher's broom extract, grapefruit oil, pomegranate and bugleweed extract, in a concentration range of 0.001% to 10.0% w/w., e.g., 0.01% to 10.0% w/w.

The vasoconstrictor formulation can also include one or more inactive ingredients, such as aloe vera juice, distilled water, cetyl alcohol, glyceryl stearate/PEG-100 stearate, sodium palmitoyl proline, sodium PCA, cyclopentasiloxane, dimethicone crosspolymer and other excipients known to those skilled in the art for use in formulating pharmaceutical preparations.

The vasoconstrictor formulation can further include substances to improve penetration or bioavailability of the active vasoconstrictor ingredients. For example, the formulation may include one or a combination of phospholipids, fatty acids, chemical penetration enhancers, and binding components that result in enhanced diffusion of the active ingredient into and through the stratum corneum. Substances which improve the penetration or bioavailability of active ingredients in topical formulations are known to those of ordinary skill in the art.

Optionally, the process of FIG. 1 or FIG. 2 can be repeated one or more times. Alternately, steps 110 and 120 may be repeated for a given number of cycles prior to applying vasoconstrictor (step 130).

Optionally, subsequent to step 130, the vasoconstrictor formulation can be re-applied after the process of FIG. 1 or FIG. 2 is complete to help maintain the benefits of the treatment. For example, a healthcare provider may instruct a patient to apply a vasoconstrictor composition on a periodic basis after treatment (e.g., one or more times daily). The vasoconstrictor formulation used subsequent to the first application of step 130 can be the same formulation as used in vasoconstriction treatment step 130, or can be one or more of the different vasoconstrictor formulation embodiments described above.

EXAMPLE 1

A clinical study was undertaken in order to demonstrate the effectiveness of the method of FIG. 2 in improving the outcome of laser/photo facial treatments. In the study, 16 patients with moderate facial redness served as their own test subject and control.

Prior to treatment, the right and left side of the face were digitally photographed using the VISIA™ Complexion Analysis System (Canfield Scientific, Fairfield N.J.). The VISIA™ system has the ability to visualize skin conditions related to abnormal melanin concentrations or vascular disorders. Visualized abnormalities include conditions such as sun damage, rosacea, melasma, telangiectasia and others.

For the clinical trial in this example the vasodilator composition contained water, arginine HCl, urea, glycerin, hydroxyethylcellulose, allantoin, methylisothiazolinone. The percentage of each reagent in the vasodilation composition is shown in Table 1 on a weight/weight basis. This vasodilation composition had a pH of 5.1.

TABLE 1

| Component | Percentage (w/w) |
| --- | --- |
| Allantoin | 0.25 |
| Optiphen MIT | 0.12 |
| Arginine HCl | 2.6 |
| Ginger Extract H5955 WS | 6 |
| *Ginkgo Biloba* Extract H5957 WS | 6 |
| Hawthorn Extract H5958 WS | 6 |
| Urea | 6 |
| Glycerin | 5 |
| Cellosize QP52000 | 0.6 |
| Water | 67.43 |
| Total: | 100 |

In all cases, a layer of pre-energy treatment vasodilating composition was applied to the left side of the face and gently massaged into the skin. No pre-treatment composition was applied to the right side. After 10 minutes of waiting for vasodilation to occur, each patient was treated with either a broad-band light source centered at 560 nm or a Nd Yag Laser at 1064 nm on both sides of the face. Treatments generally lasted for 15 minutes. The irradiation energy varied from 13 to 160 Joules.

The wavelength of the irradiation was determined by a variety of factors, including the type of flushing the patient experiences, the individual's tolerance for pain and the patient's response to the treatment. For example, if the patient had discrete veins that could be traced for treatment, the 1064 wavelength was used since that is a pinpoint laser used for tracing vessels. If the patient had more flushing than discrete vessels, the skin was irradiated with pulsed light at 560 nm because this treatment is believed to be more effective toward flushing.

The energy selected for the treatment was selected based on patient tolerance and wavelength, with patient pain tolerance being the primary factor. The energy goal was 14-16 Joules for the 560 initial treatment. When using the 1064 wavelength, the starting point was generally 160 Joules. If the patient tolerated the higher wavelengths well and the practitioner believed that the treatment was not providing an ideal response, the energy level was increased. Often patient discomfort prevents treating at higher energy level without topical anesthetic. Energy treatments for each patient are set forth in Table 2.

TABLE 2

| Patient No. | Joules | Wavelength |
|---|---|---|
| 1 | 14 | 560 |
| 2 | 14 | 560 |
| 3 | 15 | 560 |
| 4 | 13 | 560 |
| 5 | 160 | 1064 |
| 6 | 14 | 560 |
| 7 | 160 | 1064 |
| 8 | 160 | 1064 |
| 9 | 160 | 1064 |
| 10 | 14 | 560 |
| 11 | 14 | 560 |
| 12 | 155 | 1064 |
| 13 | 14 | 560 |
| 14 | 14 | 560 |
| 15 | 14 | 560 |
| 16 | 13 | 560 |

*560 = BBL Handpiece
*1064 = Nd Yag Laser

Immediately after the treatment the post-treatment vasoconstricting composition was applied to the left side of the face and gently massaged into the skin. No vasoconstricting composition was applied to the right side.

The vasoconstrictor composition used in the example clinical trial contained phytonin, aloe vera juice, arnica extract, cypress extract, Solomon's seal extract, glyceryl stearate and peg-100 stearate, sodium palmitoyl proline, nymphaea alba flower extract, cyclomethicone, stearic acid, glycerin, cetyl alcohol, butcher's broom extract, bugleweed extract, triethanolamine, pomegranate oil, allantoin, methylisothiazolinone, grapefruit oil, acrylates/c10-30 alkyl acrylate crosspolymer. As detailed in Table 3, below, the composition was formulated from four parts and had a pH of 6.5. The percentage of each reagent in the vasoconstriction composition is shown in Table 3 on a weight/weight basis.

TABLE 3

| | Percentage (w/w) |
|---|---|
| Part A | |
| Cetyl Alcohol | 1 |
| Arlacel 165 | 4 |
| Stearic Acid | 2 |
| Sepicalm VG | 3 |
| Pomegranate Oil | 0.3 |
| Part B | |
| DC 345 | 3 |
| White Grapefruit Oil | 0.1 |
| Part C | |
| Butcher's Broom Sol. | 1 |
| Bugleweed Sol. | 1 |
| Phytotonin | 10 |
| Optiphen MIT | 0.12 |
| Part D | |
| Allantoin | 0.25 |
| Pemulen TR-1 | 0.1 |
| Glycerine | 2 |
| TEA | 1 |
| *Aloe* Juice | 71.13 |
| Total: | 100 |

Each patient was advised to continue to apply the vasoconstricting composition to the left side of the face and gently massage it into the skin twice a day for four weeks.

At the end of four weeks, the patients returned to the clinic to have digital photographs taken of both the left and right sides of the face using the VISIA™ imaging system described above.

Outcomes were measured as a percentage of enhanced reduction of rosacea or broken capillaries by patient questionnaire, and by measuring the appearance of vascular lesions on the left (treated) side of the patient's face as compared to the right (untreated) control area of the patient's face using the VISIA™ system.

The patients each filled out a questionnaire specifically designed to allow patients to evaluate their overall improvement. The results are illustrated in Table 4.

TABLE 4

Results of Patient Reporting

| | % of Patients Reporting Result |
|---|---|
| Reporting a reduction in rosacea-induced facial redness | 93% |
| Reporting a reduction in post treatment swelling and redness | 80% |
| Reporting that skin felt smoother | 93% |
| Reporting a reduction in pimples/breakouts | 87% |
| Reporting an allergic reaction | 0% |

The data was also analyzed by the software included with the VISIA™ imaging system; the results are illustrated in FIG. 3 and in Table 5.

FIG. 3 is a chart showing the results of a clinical trial of an embodiment of the invention, each column to be understood as (1) patient number; (2) the date of VISIA™ measurement prior to treatment; (3) the date of treatment; (4) the date of VISIA™ measurement after treatment; (5) number of reds in treated (left) area before treatment; (6) number of reds in treated (left) area after treatment; (7) percent change in number of reds in treated (left) area before versus after treatment;

(8) evaluation of improvement in treated (left) area by VISIA™; (9) evaluation of improvement in treated (left) area by photograph; (10) number of reds in untreated (right) area before treatment; (11) number of reds in untreated (right) area after treatment; (12) percent change in number of reds in untreated (right) area before versus after treatment; (13) evaluation of improvement in untreated (right) area by VISIA™; (14) evaluation of improvement in untreated (right) area by photograph; and (15) evaluation of treated versus untreated areas. "Number of reds" refers to the quantification of the VISIA™ Red Image Analysis, where 'Red' indicates vascular structures.

TABLE 5

Results of VISIA ™ COMPUTER ANALYSIS

| | |
|---|---|
| Improvement in facial redness with applied compositions | 21% |
| Improvement in facial redness without applied compositions | 13% |
| Increased effectiveness of the laser treatment | 62% |
| Reduction in facial flushing when compared to side without applied composition treatments | 110% |
| Overall increase in effectiveness of the treatment | 62-110% |

Patients stated that they healed faster on the treated side of their faces, felt that the texture of the skin was improved on the treated side and felt less discomfort after the laser procedure on the treated side of the face.

The outcome of the clinical study demonstrates the effectiveness of the vasodilating and vasoconstricting compositions described herein as agents to improve the outcome of laser treatments for reducing facial redness. This may result in a reduction in rosacea symptoms and an increase in patient satisfaction.

EXAMPLE 2

The compositions of the invention can be supplied in the form of a kit. The kit can be supplied to a patient, or to a health care provider or cosmetologist treating a patient. The kit can include, without limitation, a first topical skin formulation including a vasodilation composition, and a second topical skin formulation including a vasoconstriction composition. The kit can include written instructions for use, by or on a patient, of the first topical skin formulation prior to receipt by the patient of an ischemia-inducing treatment and of the second topical skin formulation after receipt by the patient of an ischemia-inducing treatment. Other components can optionally be added to the kit, such as topical compositions to be applied while inducing ischemia, such as, e.g., a pain medication in a topical formulation. Vasodilation compositions and vasoconstriction compositions useful in such a kit are prepared according to the methods set forth above, and are preferably supplied in the kit in an amount suitable for a single regimen. In another embodiment, the kit can further include a energy source device, e.g., a laser, a high-intensity light, or an ultrasound transducer.

The embodiments of the invention described above are intended to be merely exemplary; numerous variations and modifications will be apparent to those skilled in the art. All such variations and modifications are intended to be within the scope of the present invention as defined in any appended claims.

The invention claimed is:

1. A method for treating an affected skin region of a patient having a skin disorder, the method comprising:
   a) first applying a vasodilation composition to the affected skin region of the patient, said affected skin region exhibiting a skin disorder characterized by at least one abnormal blood vessel, wherein said blood vessel comprises a tissue architecture,
   b) waiting for a time sufficient to allow vasodilation of the at least one abnormal blood vessel,
   c) then, non-invasively disrupting the tissue architecture of the at least one abnormal blood vessel, and
   d) subsequent to disrupting the tissue architecture, applying a vasoconstriction composition comprising bugleweed extract to the affected skin region so as to cause vasoconstriction and collapse of the at least one abnormal blood vessel.

2. The method of claim 1, wherein said skin disorder is rosacea.

3. The method of claim 1, wherein said skin disorder is telangiectasia.

4. The method of claim 1, wherein said skin disorder comprises at least one vascular lesion.

5. The method of claim 1, wherein said skin disorder is selected from the group consisting of spider veins, varicose veins, actinically damaged skin, venous hypertension, Poikiloderma vasculare atrophicans, vascular malformations, and hemangioma.

6. The method of claim 1, wherein said vasodilation composition comprises arginine.

7. The method of claim 6, wherein said vasodilation composition further comprises tolazoline.

8. The method of claim 1, wherein said vasodilation composition comprises methyl nicotinate.

9. The method of claim 1, wherein said vasodilation composition comprises tolazoline.

10. The method of claim 1, wherein said vasodilation composition comprises sodium nitroprusside.

11. The method of claim 1, wherein said vasodilation composition comprises arginine HC1, urea, glycerin, hydroxyethylcellulose, allantoin, and methylisothiazolinone.

12. The method of claim 1, wherein said non-invasive disruption comprises non-invasively inducing ischemia of said at least one abnormal blood vessel.

13. The method of claim 1, wherein said non-invasive disruption comprises selectively heating said abnormal blood vessels by raising the temperature of said abnormal blood vessels relative to the temperature of surrounding tissue.

14. The method of claim 1, wherein said non-invasive disruption comprises exposing said affected skin region to electromagnetic radiation.

15. The method of claim 1, wherein said non-invasive disruption is by photothermolysis.

16. The method of claim 1, wherein said non-invasive disruption comprises exposing said affected skin region to ultrasound.

17. The method of claim 16, wherein said vasoconstriction composition comprises phytonin, aloe vera juice, arnica extract, cypress extract, Solomon's seal extract, glyceryl stearate, peg-100 stearate, sodium palmitoyl proline, nymphaea alba flower extract, cyclomethicone, stearic acid, glycerin, cetyl alcohol, butcher's broom extract, bugleweed extract, triethanolamine, pomegranate oil, allantoin, methylisothiazolinone, grapefruit oil, and an alkyl acrylate crosspolymer.

18. The method according to claim 1, wherein the waiting includes monitoring for indications that blood vessels have dilated prior to proceeding with the non-invasively disrupting.

* * * * *